United States Patent
Kono et al.

(10) Patent No.: US 8,215,829 B2
(45) Date of Patent: Jul. 10, 2012

(54) METHOD OF ANALYZING THERMAL STRESS ACCORDING TO FILLING FACTOR OF FILLER IN RESIN

(75) Inventors: Tsutomu Kono, Chiyoda-ku (JP); Masayuki Mino, Chiyoda-ku (JP); Hidehiro Takeshima, Chuo-ku (JP); Youkou Ito, Chuo-ku (JP); Tomoko Goi, Chuo-ku (JP)

(73) Assignee: Elpida Memory, Inc., Tokyo (JP)

( * ) Notice: Subject to any disclaimer, the term of this patent is extended or adjusted under 35 U.S.C. 154(b) by 424 days.

(21) Appl. No.: 12/604,009

(22) Filed: Oct. 22, 2009

(65) Prior Publication Data

US 2010/0103977 A1    Apr. 29, 2010

(30) Foreign Application Priority Data

Oct. 29, 2008 (JP) ................................ 2008-278269

(51) Int. Cl.
  *G01N 25/00* (2006.01)
(52) U.S. Cl. ...................... 374/57; 374/5; 374/7; 374/43
(58) Field of Classification Search .................. 374/57, 374/5, 7, 43
See application file for complete search history.

(56) References Cited

U.S. PATENT DOCUMENTS

| | | | | | |
|---|---|---|---|---|---|
| 3,693,458 | A | * | 9/1972 | Odell | ............................... 73/866 |
| 3,842,654 | A | * | 10/1974 | Bechtel | ........................... 374/51 |
| 3,934,452 | A | * | 1/1976 | Prevorsek et al. | .............. 374/47 |
| 6,896,405 | B2 | * | 5/2005 | Osone et al. | .................... 374/43 |
| 2007/0137323 | A1 | * | 6/2007 | Floyd et al. | ..................... 73/866 |

FOREIGN PATENT DOCUMENTS

JP   2006-205740 A   8/2006

* cited by examiner

*Primary Examiner* — Lisa Caputo
*Assistant Examiner* — Mirellys Jagan
(74) *Attorney, Agent, or Firm* — Sughrue Mion, PLLC

(57) ABSTRACT

A method of analyzing thermal stress includes calculating a distribution of the number of fillers in a composite integrally molded product by using physical property values of resin material containing fillers, and determining a coefficient of linear expansion of the resin material in the composite integrally molded product, that is used as an input condition of a thermal stress analysis, based on the distribution of the number of the fillers.

10 Claims, 7 Drawing Sheets

METHOD OF ANALYZING THERMAL STRESS ACCORDING TO FILLING FACTOR OF FILLER IN RESIN

This application is based upon and claims the benefit of priority from Japanese Patent Application No. 2008-278269 filed on Oct. 29, 2008, the content of which is incorporated by reference.

BACKGROUND OF THE INVENTION

1. Field of the Invention

The present invention relates to a method of analyzing thermal stress, a method of analyzing a resin flow and an analysis processing apparatus of an electronic part including a package using resin material.

2. Description of Related Art

An example of techniques of evaluating an amount of warpage deformation of an electronic part integrally molded with thermosetting resin such as a semiconductor package is disclosed in Japanese Patent Laid-Open No. 2006-205740. This document describes a method for calculating an amount of warpage deformation using results such as a modulus of elasticity and resin temperature variation calculated by flow analysis using thermosetting resin as input values of a structural analysis.

In order to meet demands for a reduction in thickness or size of electronic apparatuses such as mobile phones in recent years, a so-called "PonP (Package on Package) structure" and a stack structure in which chips are stacked in the thickness direction are used for semiconductor packages. Therefore, in manufacturing semiconductor packages, gaps through which resin flows are becoming smaller. Resin materials are generally filled with inorganic filler such as talc or silica. As gaps through which resin flows become smaller, there occurs a problem in which a filling factor of the filler varies depending on places in the package.

Furthermore, when the filling factor of the filler varies, its coefficient of linear expansion also varies. In correspondence with the coefficient of linear expansion, the amount of warpage deformation of a thin package caused by a temperature variation also varies. In order to accurately evaluate the amount of warpage deformation of the thin package caused by a temperature variation, it is necessary to calculate a filler filling factor using flow analysis of resin in different places of the package and to predict the amount of warpage deformation through a structural analysis using a coefficient of linear expansion corresponding to the filler filling factor.

However, no prediction technique for the amount of warpage deformation by a structural analysis using a coefficient of linear expansion corresponding to a filler filling factor is so far known. Therefore, prototype molding needs to be repeated to select resin material including a structure and a filler filling factor that allow the amount of warpage deformation of a semiconductor package to be suppressed.

SUMMARY

In one embodiment, there is provided a method of analyzing thermal stress that includes calculating a distribution of the number of fillers in a composite integrally molded product by using physical property values of resin material containing fillers, and determining a coefficient of linear expansion of the resin material in the composite integrally molded product, that is used as an input condition of a thermal stress analysis, when the based on the distribution of the number of the fillers.

BRIEF DESCRIPTION OF THE DRAWINGS

The above features and advantages of the present invention will be more apparent from the following description of certain preferred embodiments taken in conjunction with the accompanying drawings, in which.

DETAILED DESCRIPTION OF THE PREFERRED EMBODIMENTS

The invention will be now described herein with reference to illustrative embodiments. Those skilled in the art will recognize that many alternative embodiments can be accomplished using the teachings of the present invention and that the invention is not limited to the embodiments illustrated for explanatory purposes.

The present embodiment is an analysis method relating to a molding technique using resin material filled with filler such as talc or silica. Furthermore, the present embodiment will be explained using a case of a three-dimensional flow analysis method when evaluating, in an electronic part such as a semiconductor package integrally molded by means of transfer molding using the above described resin material, an amount of warpage deformation due to differences in coefficients of linear expansion between chips, a substrate and resin material making up the semiconductor package when the temperature is changed.

Hereinafter, embodiments of the present invention will be explained with reference to the accompanying drawings.

Figure 1A:
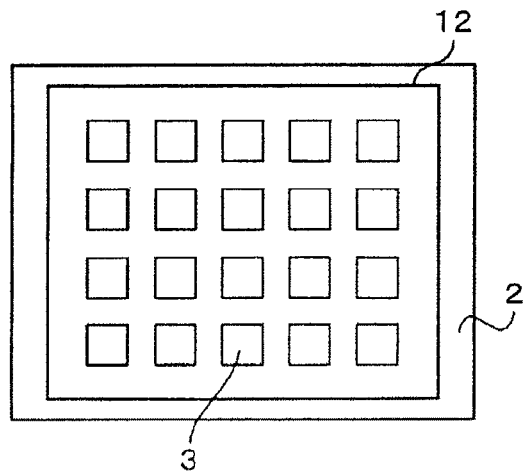
FIG. 1A is a plan view showing an example of a structure before molding of a semiconductor package that includes chips, a substrate and resin material that are to be analyzed.
Figure 1B:
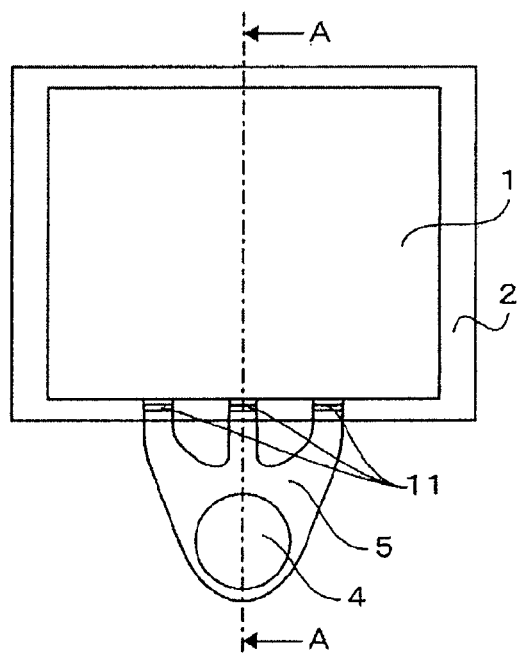
FIG. 1B is a plan view showing a structure after molding of the semiconductor package shown in FIG. 1A.
Figure 1C:
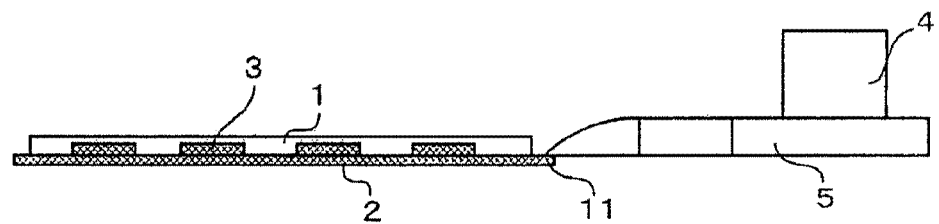
FIG. 1C is a cross-sectional view of A-A of the semiconductor package shown in FIG. 1B.

FIG. 1A shows a structure with a plurality of chips 3 mounted on substrate 2, which is to be analyzed. FIG. 1A is a plan view of the structure before molding. FIG. 1B is a plan view of the structure after applying molding to the structure shown in FIG. 1A. The inside of mold region 12 shown in FIG. 1A becomes a package and substrate 2 and chip 3 are integrally molded with resin material 1 as shown in FIG. 1B. FIG. 1C is a cross-sectional view of the structure shown in FIG. 1B.

Here, molding will be explained briefly. Substrate 2 shown in FIG. 1A is clamped by a die, solid-state resin is placed in pot 4 of the die, the solid-state resin is heated and pressurized in pot 4 and resin material 1 is poured into cull 5. Resin material 1 is heated also in cull 5 to reduce a viscosity of resin material 1, resin material 1 is filled into the package from gates 11. Thus, chips 3 and substrate 2 are integrally molded with resin material 1. The molded package includes a plurality of chips 3 and is provided by being divided into units of substrate 2 region in which each chip 3 electrically operates.

Resin material 1 of the semiconductor package is filled with inorganic filler such as silica to reduce its coefficient of linear expansion. For this reason, the coefficient of linear expansion of resin material 1 varies depending on the filling factor of the filler contained in resin material 1 in the package.

Next, an analysis processing apparatus for predicting a filler filling factor in a resin molding process through a resin flow analysis and executing a thermal stress analysis in consideration of a coefficient of linear expansion according to the filler filling factor after molding will be explained.

Figure 2A:
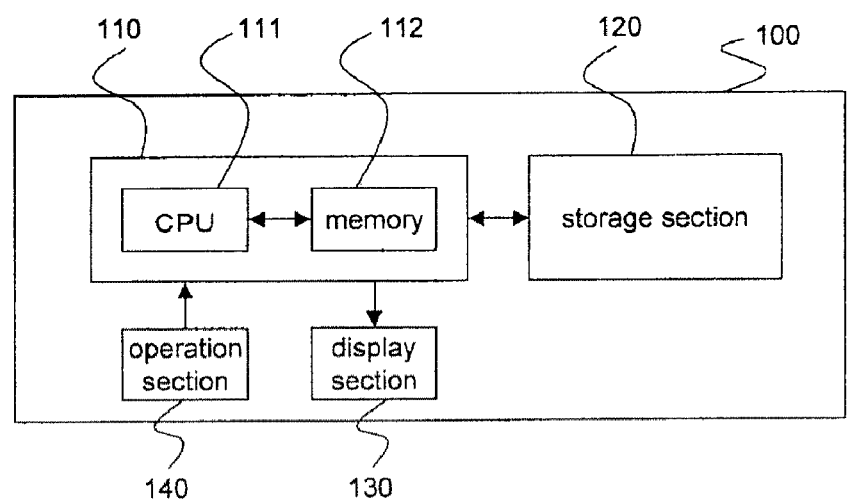
FIG. 2A is a block diagram showing a configuration example of an analysis processing apparatus of the present embodiment.

FIG. 2A is a block diagram showing a configuration example of the analysis processing apparatus according to the present embodiment.

As shown in FIG. 2A, analysis processing apparatus 100 is provided with storage section 120, display section 130, control section 110 and operation section 140. Control section 110 is provided with memory 112 for storing an analysis program and CPU (Central Processing Unit) 111 that executes processing according to the analysis program. Storage section 120 includes an HD (Hard Disk) drive and MO (Magneto Optical Disk) drive. Storage section 120 stores information such as equations and data necessary for an analysis beforehand. Operation section 140 includes input devices such as a keyboard and mouse. The contents of processing according to the analysis program will be explained using FIG. 3.

Figure 2B:
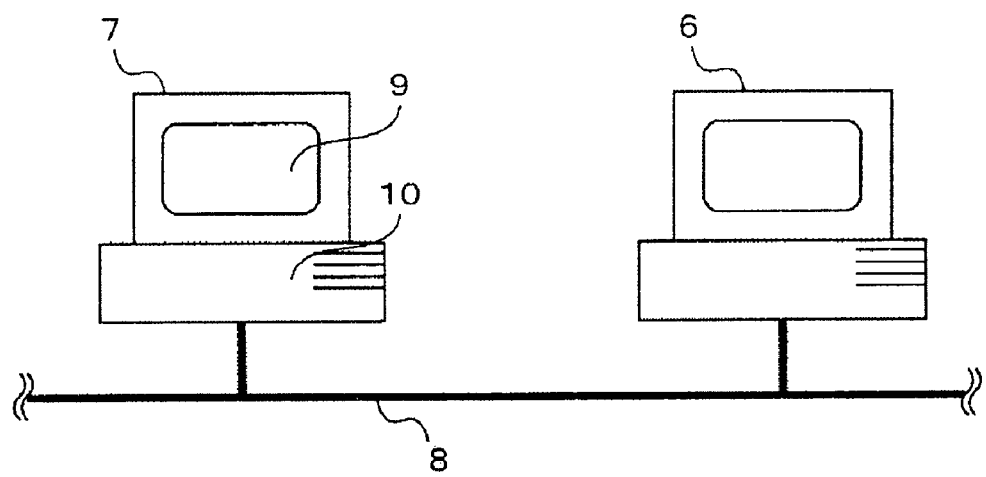
FIG. 2B is a block diagram showing a configuration example of an analysis system of the present embodiment.

An analysis system including two information processing apparatuses may also be made to perform the thermal stress analysis of the present embodiment. FIG. 2B is a block diagram showing a configuration example of the analysis system of the present embodiment.

As shown in FIG. 2B, the analysis system has calculation apparatus 6 and calculation apparatus 7. Calculation apparatus 7 is provided with main body 10 having a storage section including an HD drive and MO drive and a control section that executes processing according to a program, display section 9 and an operation section (not shown). The operation section (not shown) includes input devices such as a keyboard and mouse (not shown). Since calculation apparatus 6 has a configuration similar to that of calculation apparatus 7, detailed explanations thereof will be omitted.

As shown in FIG. 2B, calculation apparatus 6 and calculation apparatus 7 are connected together via LAN (Local Area Network) 8. Calculation apparatus 6 transmits CAD (Computer Aided Design) data that has been created to calculation apparatus 7 via LAN 8. The CAD data corresponds to data showing the structure to be analyzed before molding shown in FIG. 1A. Upon receiving the CAD data from calculation apparatus 6, calculation apparatus 7 executes processing according to the procedure shown in FIG. 3, stores the result in the storage section (not shown) and then displays the result on display section 9.

Hereinafter, a case will be explained where the analysis method of the present embodiment is executed by analysis processing apparatus 100. An analysis procedure by analysis processing apparatus 100 of the present embodiment will be explained with reference to FIG. 3.

Figure 3:
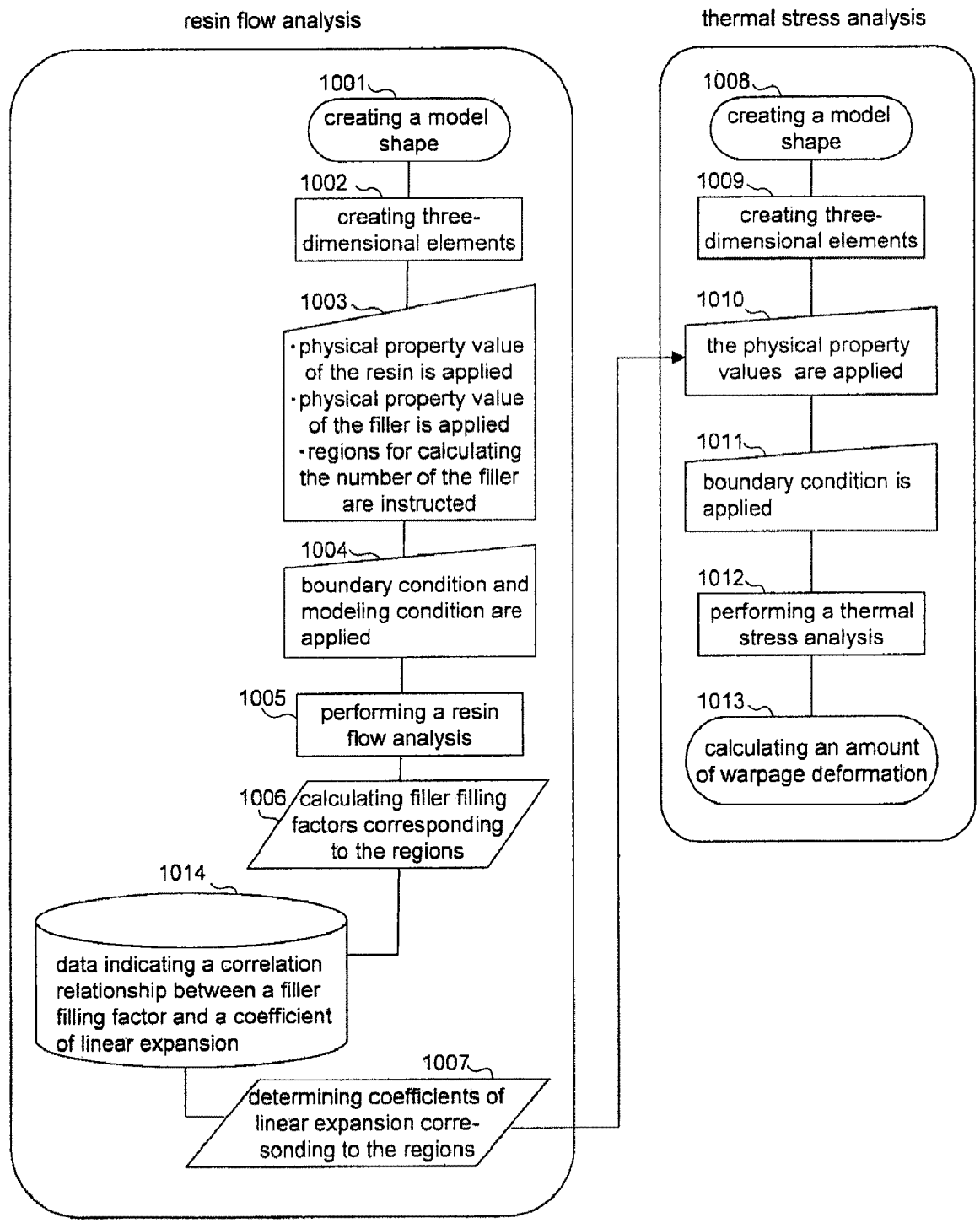
FIG. 3 is a flowchart showing an analysis procedure of the present embodiment.

FIG. 3 is a flowchart showing a processing procedure executed by the analysis processing apparatus of the present embodiment according to an analysis program.

First, a procedure for a resin flow analysis will be explained.

In model shape creation processing in step 1001, control section 110 reads data of a model to be analyzed specified by the operator via operation section 140 from storage section 120. The data of the model to be analyzed here is data indicating respective three-dimensional spaces of pot 4, cull 5, gates 11 and the resin portion in the package of the portion through which resin material 1 to be analyzed flows.

Next, in three-dimensional solid element creation processing in step 1002, control section 110 decomposes the shape based on the data read in step 1001 into a plurality of specific spaces. Here, it is assumed that the specific spaces are finite elements of three-dimensional solid. Next, control section 110 creates a shape data of each finite element.

Next, in physical property value input processing in step 1003, when using a density, coefficient of thermal conductivity, specific heat and thermosetting resin, which are physical property values of resin material 1 that is to be analyzed, the operator inputs heat generation Equations 1 to 5 and viscosity Equations 6 to 9, as shown below, via operation section 140. Instead of inputting these equations in step 1003, the operator may register the information on these equations with storage section 120 beforehand, input a read instruction to operation section 140 and thereby cause control section 110 to read these equations from storage section 120.

Furthermore, control section 110 causes display section 130 to display a message instructing the input of such information to urge the operator to input the filling factor, density and diameter of the filler in the resin material placed in pot 4 in an initial state. When the information is inputted through operation section 140, control section 110 stores the data in storage section 120. Here, assuming that the filler has a spherical shape, the diameter distribution of the sphere or the like may be inputted.

In the equations shown below, various parameters will be defined as follows, A: reaction rate; t: time; T: temperature; dA/dt: reaction speed; $K_1$, $K_2$: coefficients which become functions of temperature; N, M, Ka, Ea, Kb, Eb: coefficients intrinsic to material; Q: heat value until arbitrary time; $Q_0$: total heat value until reaction end; dQ/dt: heat generation speed; $\eta$: viscosity; $\eta_0$: initial viscosity; $t_0$: gelation time; T: temperature; a, b, d, e, f, g: constants intrinsic to material.

$$dA/dt = (K_1 + K_2 A^M)(1-A)^N \quad \text{(Equation 1)}$$

$$K_1 = K_a \exp(-E_a/T) \quad \text{(Equation 2)}$$

$$K_2 = K_b \exp(-E_b/T) \quad \text{(Equation 3)}$$

$$A = Q/Q_0 \quad \text{(Equation 4)}$$

$$dQ/dt = Q_0(K_1 + K_2 A^M)(1-A)^N \quad \text{(Equation 5)}$$

$$\eta = \eta_0((t+t_0)/(t-t_0))C(T) \quad \text{(Equation 6)}$$

$$\eta_0 = a \exp(b/T) \quad \text{(Equation 7)}$$

$$t_0 = d \exp(e/T) \quad \text{(Equation 8)}$$

$$C(T) = f/T - g \quad \text{(Equation 9)}$$

Furthermore, in step 1003, when the package range is divided into two or more regions so as to output the number of fillers to each of predetermined regions after execution of the analysis, the operator inputs each region to control section 110 via operation section 140. In this step, a region which becomes the output unit of the number of fillers is set.

Next, in boundary condition and molding condition input processing in step 1004, control section 110 causes display section 130 to display a message instructing input of the information to urge the operator to input a die temperature, initial temperature of resin and pressure applied to resin. When the information is inputted via operation section 140, control section 110 stores the data in storage section 120.

Next, the operator inputs an instruction for starting an analysis and information on an increment of the initial time to control section 110 via operation section 140. In step 1005, control section 110 reads the equation of continuity (Equation 10), Navier-Stokes Equations 11 to 13 and energy conservation law (Equation 14) stored beforehand in storage section 120 from storage section 120 based on the inputted instruction.

Control section 110 then reads the input data stored so far from storage section 120 and assigns the increment of the initial time, die temperature, initial temperature of the resin, pressure applied to resin, density of the resin material, specific heat, coefficient of thermal conductivity, heat generation Equations 1 to 5, viscosity Equations 6 to 9, filling factor, density and diameter of the filler in the resin material placed in pot 4 in an initial state to (Equation 10) to (Equation 14) and calculates the speed, pressure, temperature and viscosity accompanying the flow of resin and filler caused by the pressurization of resin. Control section 110 then saves the calculation result in association with the positions of the finite elements in storage section 120.

Here, the respective symbols represent the following, $\rho$: density; u: x-direction speed; v: y-direction speed; $\omega$: z-direction speed; T: temperature; P: pressure; t: time; $\eta$: viscosity; Cp: specific heat at constant pressure; $\beta$: volume expansion coefficient; $\lambda$: coefficient of thermal conductivity.

$$\frac{\partial \rho}{\partial t} + \frac{\partial (\rho u)}{\partial x} + \frac{\partial (\rho v)}{\partial y} + \frac{\partial (\rho \omega)}{\partial z} = 0 \quad \text{(Equation 10)}$$

$$\rho \frac{\partial u}{\partial t} = \rho g_x - \frac{\partial P}{\partial x} + \frac{\partial}{\partial x}\left(2\eta \frac{\partial u}{\partial x}\right) + \frac{\partial}{\partial y}\left(\eta\left(\frac{\partial v}{\partial x} + \frac{\partial u}{\partial y}\right)\right) + \frac{\partial}{\partial z}\left(\eta\left(\frac{\partial u}{\partial z} + \frac{\partial \omega}{\partial x}\right)\right) - \rho\left(u\frac{\partial u}{\partial x} + v\frac{\partial u}{\partial y} + \omega\frac{\partial u}{\partial z}\right) \quad \text{(Equation 11)}$$

$$\rho \frac{\partial v}{\partial t} = \rho g_y - \frac{\partial P}{\partial y} + \frac{\partial}{\partial y}\left(2\eta \frac{\partial v}{\partial y}\right) + \frac{\partial}{\partial x}\left(\eta\left(\frac{\partial u}{\partial y} + \frac{\partial v}{\partial x}\right)\right) + \frac{\partial}{\partial z}\left(\eta\left(\frac{\partial \omega}{\partial y} + \frac{\partial v}{\partial z}\right)\right) - \rho\left(u\frac{\partial v}{\partial x} + v\frac{\partial v}{\partial y} + \omega\frac{\partial v}{\partial z}\right) \quad \text{(Equation 12)}$$

$$\rho \frac{\partial \omega}{\partial t} = \rho g_z - \frac{\partial P}{\partial z} + \frac{\partial}{\partial z}\left(2\eta \frac{\partial \omega}{\partial z}\right) + \frac{\partial}{\partial y}\left(\eta\left(\frac{\partial v}{\partial z} + \frac{\partial \omega}{\partial y}\right)\right) + \frac{\partial}{\partial x}\left(\eta\left(\frac{\partial u}{\partial z} + \frac{\partial \omega}{\partial x}\right)\right) - \rho\left(u\frac{\partial \omega}{\partial x} + v\frac{\partial \omega}{\partial y} + \omega\frac{\partial \omega}{\partial z}\right) \quad \text{(Equation 13)}$$

$$\rho C_P\left(\frac{\partial T}{\partial t} + u\frac{\partial T}{\partial x} + v\frac{\partial T}{\partial y} + \omega\frac{\partial T}{\partial z}\right) = \beta T\left(\frac{\partial P}{\partial t} + u\frac{\partial P}{\partial x} + v\frac{\partial P}{\partial y} + \omega\frac{\partial P}{\partial z}\right) + \eta\gamma^2 + \lambda\left(\frac{\partial^2 T}{\partial x^2} + \frac{\partial^2 T}{\partial y^2} + \frac{\partial^2 T}{\partial z^2}\right) + \rho\frac{\partial Q}{\partial t} \quad \text{(Equation 14)}$$

In step 1006, control section 110 calculates the number of fillers N for each region set in step 1003 from the flow analysis result of resin in step 1005 and outputs the filler filling factor for each region from the result.

Here, assuming that the actual filler filling factor in resin is BW (wt %), the filler filling factor set by the analysis is CW (vol %), particle diameter is $\square_d$, and the volume of the resin portion in a certain region is V, filler filling factor G (vol %) in the certain region is expressed by Equation 15.

$$G = (N \times 4\pi/3(\square_d/2)^\wedge 3)/V \times BW/CW \quad \text{(Equation 15)}$$

Figure 4:
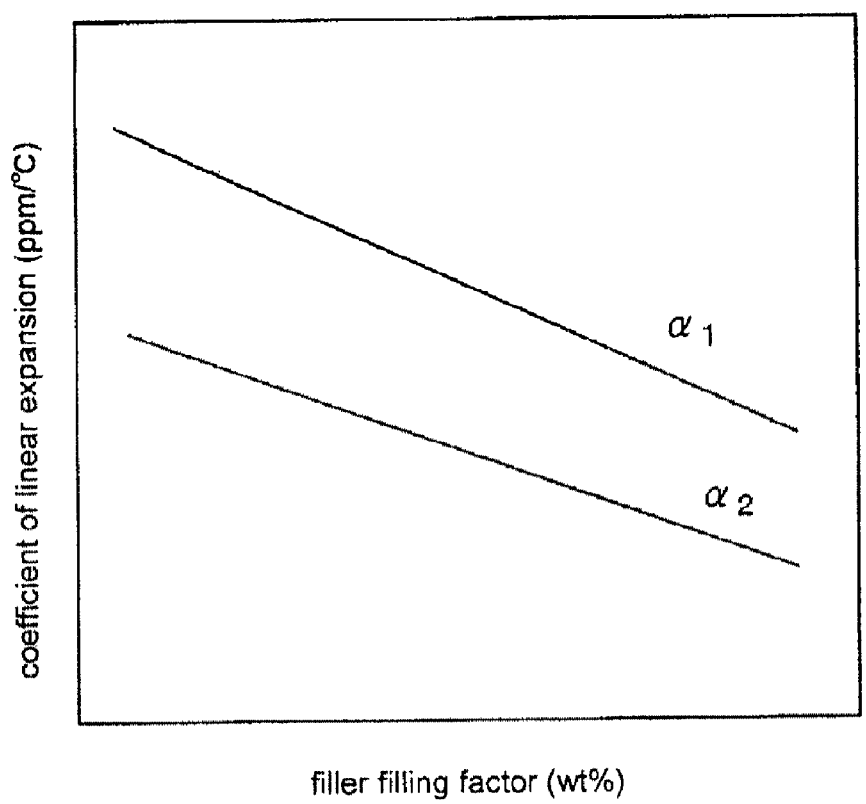
FIG. 4 shows a relationship between a particle filling factor and a coefficient of linear expansion.

Storage section 120 prestores a database in which the data of filler filling factors and coefficients of linear expansion are experimentally obtained and accumulated beforehand. In step 1007, control section 110 uses data of the filler filling factor and coefficient of linear expansion of the database to output the coefficient of linear expansion $_1$ equal to or higher than a glass transition point and the coefficient of linear expansion $a_2$ equal to or lower than the glass transition point from the filler filling factor for each region calculated by Equation 15. FIG. 4 is a graph showing a relationship between the filler filling factor and coefficient of linear expansion $\alpha_1$ equal to or higher than the glass transition point and coefficient of linear expansion $\alpha_2$ equal to or lower than the glass transition point.

Next, the procedure for thermal stress analysis will be explained with reference to FIG. 3.

When executing a thermal stress analysis, in model shape creation processing in step 1008, control section 110 reads information on a model to be analyzed specified by the operator via operation section 140 from storage section 120. The information on the model to be analyzed referred to here is information on the portions of chip 3, substrate 2 and resin material 1 making up the package that is to be analyzed.

In three-dimensional solid element creation processing in step 1009, control section 110 decomposes the shape of the data read in model shape creation step 1007 into a plurality of specific spaces. Here, suppose the specific spaces are three-dimensional solid finite elements. Next, control section 110 creates shape data of the respective finite elements.

Next, in physical property value input processing in step 1010, the operator inputs values including the density, the coefficient of thermal conductivity, the coefficient of linear expansion, the modulus of elasticity and Poisson's ratio, which are physical property values of resin material 1, chip 3 and substrate 2 to be subjected to thermal stress analysis via operation section 140. Here, as for coefficients of linear expansion of resin material 1, the values outputted in step 1007 are used as value $\alpha_1$ equal to or lower than the glass transition point and value $\alpha_2$ equal to or higher than the glass transition point for each region by referring to the graph of FIG. 4 (step 1014).

Furthermore, when the elements created in step 1009 are located spanning across a plurality of regions set in step 1003 to which the number of fillers is outputted, suppose an average of coefficients of linear expansion in those regions is used. The elements created in step 1009 may be created for each of the plurality of regions set in step 1003 to which the number of fillers is outputted.

In boundary condition input processing in step 1011, the operator inputs binding points of thermal stress analysis and thermal stress loads to control section 110 via operation section 140.

Next, the operator inputs an instruction for starting an analysis and information on the increment of the initial time to control section 110 via operation section 140. In step 1012, control section 110 reads the information on the shape stored in storage section 120 and that is divided into elements in step 1009 based on the inputted instruction, assigns the contents including the density, coefficient of thermal conductivity, coefficient of linear expansion, modulus of elasticity, Poisson's ratio, binding point and thermal stress load inputted so far to the shape divided into elements in step 1009 and calculates the stress and amount of deformation caused by differences in coefficients of linear expansion.

Next, in step 1013, control section 110 calculates and outputs the amount of warpage deformation.

EXAMPLE 1

Here, using general-purpose fluid software (FLOW-3D manufactured by FLOW SCIENCE), control section 110 was caused to execute this program and a filler distribution accompanying the flow of resin was calculated. In this case, the filler diameter was set to $\phi$ 60 μm, the filler density was set to 2500 kg/m$^3$, the density of resin material 1 was set to 1000 kg/m$^3$, specific heat was set to 1000 J/mK, coefficient of thermal conductivity was set to 0.17 W/mK, and filling factor of particles in resin was set to 5 (wt %). Furthermore, although calculations can be carried out using heat generation Equations 1 to 5 and viscosity Equations 6 to 9, the viscosity was fixed to 1 Pa·s without taking heat generation reaction into consideration here.

Figure 5A:
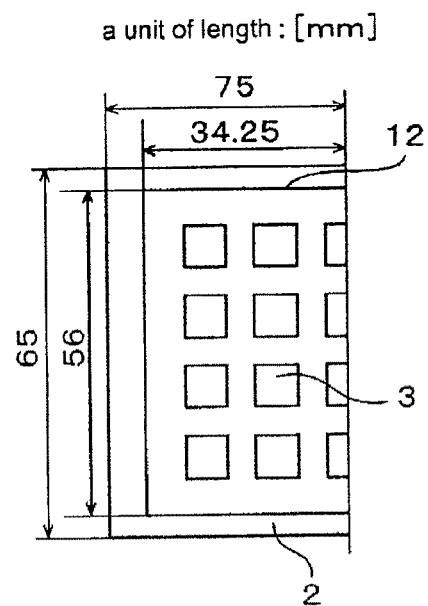
FIG. 5A shows sizes of the substrate and chips used for an analysis.
Figure 5B:
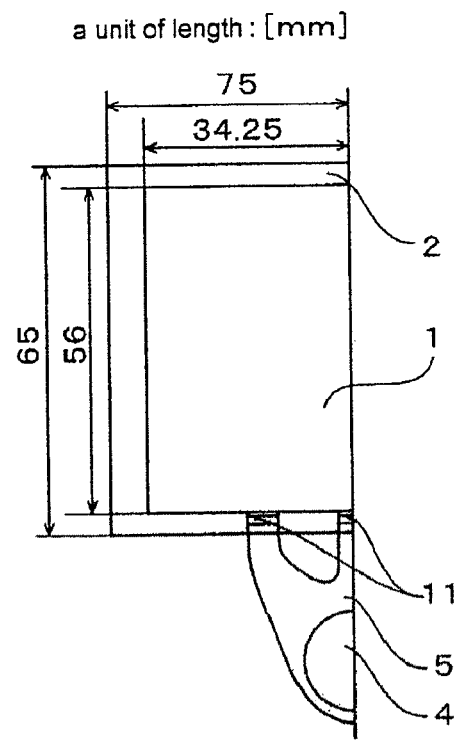
FIG. 5B shows sizes after molding with resin with respect to the substrate and chips shown in FIG. 5A.

In the calculations, a model ½ of the shape shown in FIG. 1A was used as a target and a flow analysis of resin material 1 filled with the filler was performed. The sizes of substrate 2 and chip 3 are shown in FIG. 5A. The sizes of substrate 2 and chip 3 after molding with resin are shown in FIG. 5B.

Suppose the resin thickness of the package portion in mold region 12 shown in FIG. 5A is 0.25 mm and the size of chip 3 is 7.4×6.75×0.1 mm. Here, suppose resin is charged into pot 4, resin is heated in cull 5 and then resin is charged into mold region 12 shown in FIG. 5A in the package from gates 11 and integrally molded.

Figure 6:
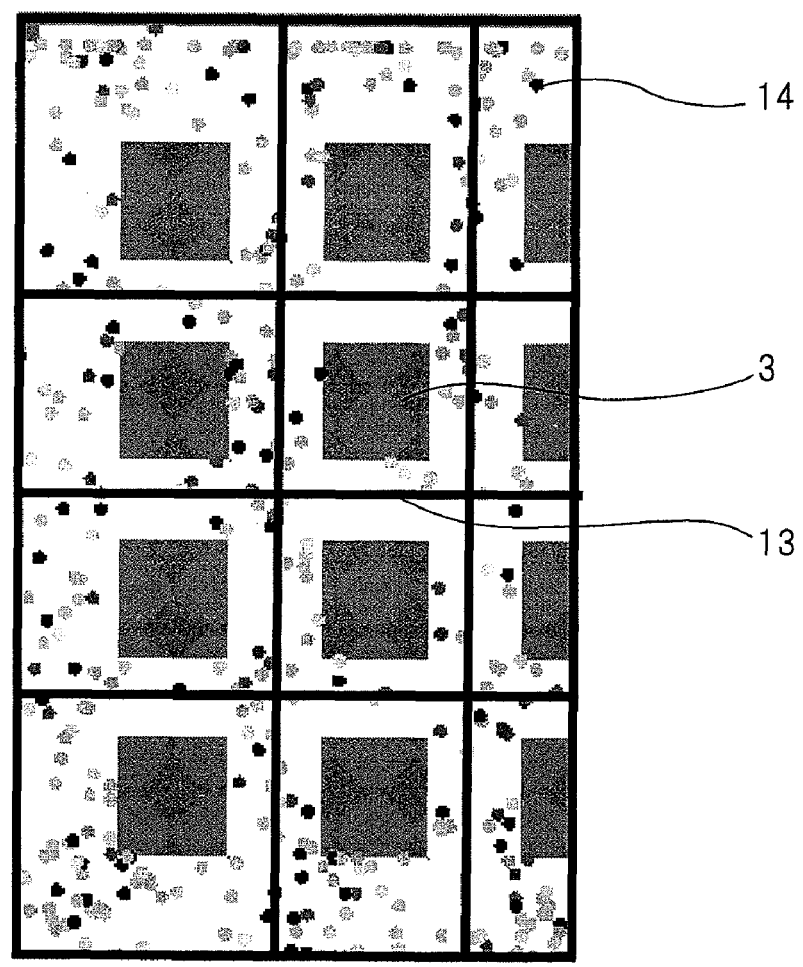
FIG. 6 shows a calculation result of filling of filler in the package.

FIG. 6 shows the result of distribution of filler 14 in the package. The operator inputs an instruction or control section 110 follows the program to virtually divide the package into a plurality of regions where each chip 3 can electrically operate by parting lines 13. Control section 110 then calculates the number of fillers 14 for each divided region. Next, control section 110 calculates a filling factor of filler 14 using the number of fillers 14 for each divided region and Equation 15. Furthermore, control section 110 calculates a coefficient of linear expansion for each divided region from the relationship between the filler filling factor and coefficient of thermal conductivity shown in FIG. 4.

Control section 110 calculates an amount of warpage deformation using the coefficient of linear expansion calculated using the number of fillers 14 as the input value of thermal stress analysis. Using general-purpose structural analysis software (LS-DYNA manufactured by LSTC) to analyze the amount of warpage deformation, control section 110 was caused to execute this program and calculations were made by modeling the portions of chip 3, substrate 2 and resin material 1 having shapes shown in FIG. 5A.

Here, the contents which include coefficient of linear expansion: 8 ppm; modulus of elasticity: 170 GPa; Poisson's ratio: 0.1; and density: 2200 kg/m$^3$ as regards chip 3, and that include coefficient of linear expansion $\alpha_1$:15 ppm and $\alpha_2$:9 ppm; modulus of elasticity: 50 GPa; Poisson's ratio: 0.2; and density: 2500 kg/m$^3$ as regards substrate 2, are inputted. Furthermore, as regards resin material 1, the contents which include modulus of elasticity: 20 GPa; Poisson's ratio: 0.3; and density: 2000 kg/m$^3$, are inputted, and the value calculated for each region from the filler filling factor obtained in FIG. 6 is used as the coefficient of linear expansion. Furthermore, a condition in which the temperature drops from 170° C. to 25° C. is used.

Figure 7:
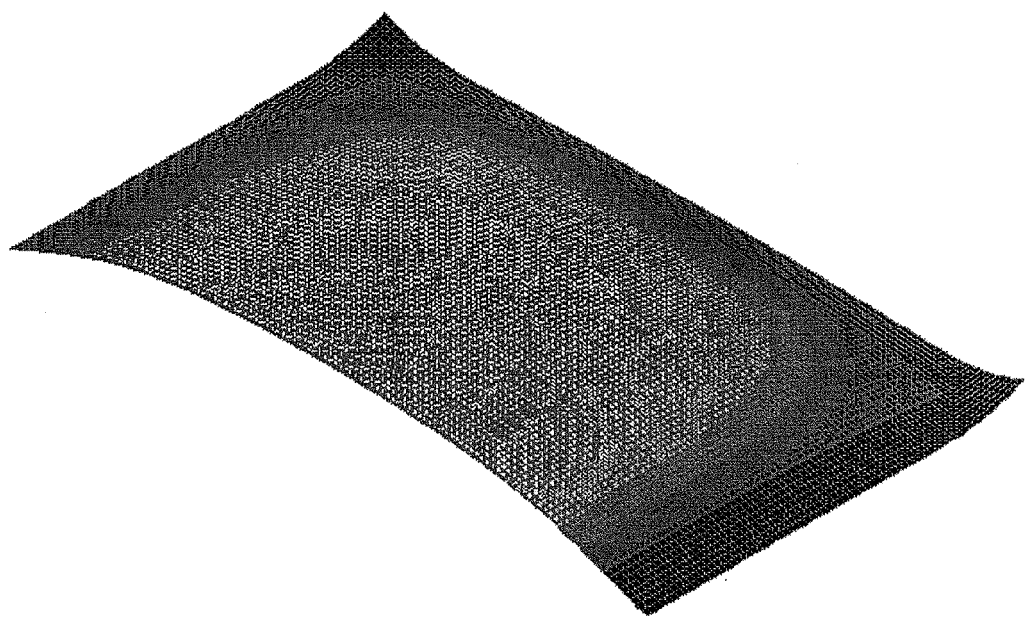
FIG. 7 shows a calculation result of the amount of warpage deformation by performing thermal stress analysis using the coefficient of linear expansion calculated from the filling factor of the filler in the package.

The analysis result of the amount of warpage deformation is shown in FIG. 7. In this way, it is possible to predict the occurrence of warpage deformation when the temperature drops from the differences in coefficients of linear expansion between a plurality of chips 3, substrate 2 and resin material 1.

Figure 8:
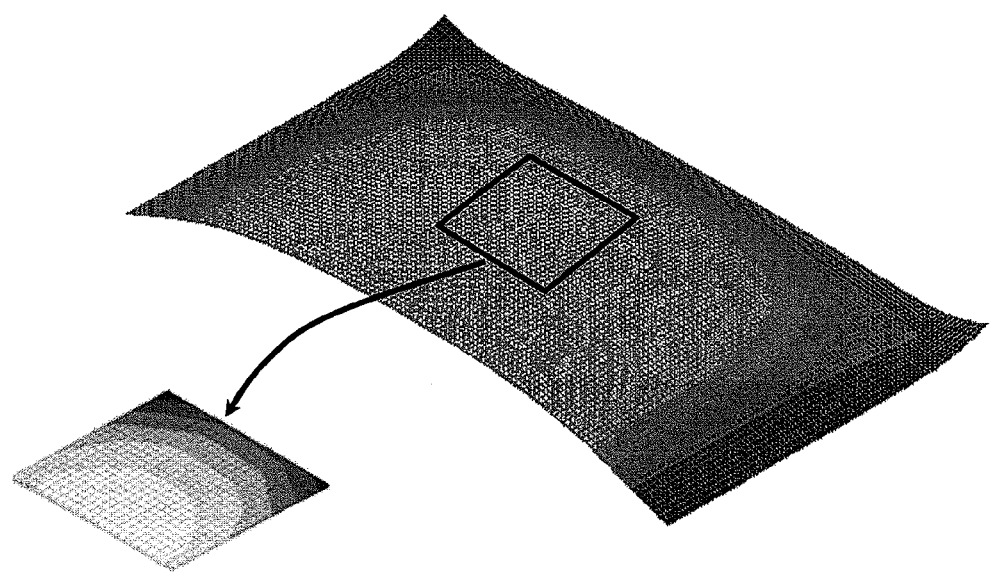
FIG. 8 shows a calculation result of the amount of warpage deformation of each region derived from the amount of warpage deformation of the entire package when the substrate region is divided into unit regions in each of which one chip can electrically operate.

The technique of predicting the amount of warpage deformation of an entire package which is made up of a plurality of chips and integrally molded using a mold has been shown here, but the present invention is not limited to this. It is also possible to calculate the amount of warpage deformation in a region where one chip can electrically operate from the amount of warpage deformation of the package which is made up of a plurality of chips shown in FIG. 7 and integrally molded. FIG. 8 shows a result of calculation of the amount of warpage deformation in each region derived from the amount of warpage deformation of the entire package when a substrate region is divided into regions in each of which one chip can electrically operate.

As shown in FIG. 8, when a region where one chip 3 can electrically operate is extracted from the package, the amount of warpage deformation of the package is reflected in the region. Therefore, it is also possible to calculate the amount of warpage deformation in a region where one chip 3 can electrically operate by taking into consideration the release of residual stress. Here, a technique of removing elements in regions other than a predetermined region is used to extract only the predetermined region from the entire analysis target.

Furthermore, it is also possible to separately use thermal stress analysis by adding a temperature atmospheric condition when a package region, where one chip 3 electrically operates, is mounted in a product, or by adding load condition that is applied to the product in which the package region is mounted, and to calculate a result including the amount of deformation and stress of the package simulating the condition in which the package is mounted in the product.

Furthermore, the present embodiment has been explained using a case where in steps 1003, 1004, 1010 and 1011 shown in FIG. 3, the operator inputs information via operation section 140 or information is stored in storage section 120 beforehand and read by control section 110, but the operator may also input the information in the above described steps or the information may be stored in storage section 120 beforehand.

The present embodiment calculates the amount of warpage deformation through structural analysis that takes into consideration the coefficients of linear expansion due to a distribution of filler filling factors in a package by performing a flow analysis using resin filled with particles simulating filler, calculating filler filling factors in different places of the package, converting the filler filling factors in different places of the package to coefficients of linear expansion using experimentally calculated data of the filler filling factors and coefficients of linear expansion and using the converted coefficients of linear expansion as input values of thermal stress analysis.

The structural analysis by taking into consideration the filler filling factors in the package and distribution of coefficients of linear expansion makes it possible to predict the amount of warpage deformation and to shorten the development period as regards design of the semiconductor package structure.

Furthermore, dividing the substrate into regions in each of which each chip can electrically operate after calculating the amount of warpage deformation of the package makes it possible to calculate the amounts of warpage deformation of individual packages.

The present invention makes it possible to optimize a package shape such as chip thickness, chip size and chip aspect ratio, and to optimize physical property values of resin material such as filler shape, filler size and resin viscosity. Since such optimizations can be realized without prototype manufacturing, the present invention provides advantages such as cost reduction and shortening of development period.

It is apparent that the present invention is not limited to the above embodiments, but may be modified and changed without departing from the scope and spirit of the invention.

What is claimed is:

1. A method of analyzing thermal stress for calculating an amount of warpage deformation of a composite integrally molded product using resin material containing fillers, the method comprising:
    calculating a distribution of the number of said fillers in said composite integrally molded product by executing a resin flow analysis using physical property values of said resin material containing fillers;
    determining a coefficient of linear expansion of said resin material in said composite integrally molded product based on said distribution of the number of said fillers; and
    calculating an amount of warpage deformation of said composite integrally molded product by executing a thermal stress analysis using said coefficient of linear expansion as an input condition of physical property values of said thermal stress analysis.

2. The method of analyzing thermal stress according to claim 1, wherein a process of calculating said distribution of the number of said fillers is to calculate the number of fillers for each of a plurality of regions by dividing said composite integrally molded product into predetermined regions, by executing said resin flow analysis, and
    a process of determining said coefficient of linear expansion is to determine said coefficient of linear expansion corresponding to each of said plurality of regions by referring to prepared data indicating a correlation relationship between a filler filling factor and a coefficient of linear expansion.

3. The method of analyzing thermal stress according to claim 1, wherein said composite integrally molded product is a package which comprises a plurality of semiconductor chips and said resin material and,
    the method further comprising dividing said package into a plurality of individual packages corresponding to said plurality of semiconductor chips after calculating said amount of warpage deformation of said entire package, and calculating an amount of warpage deformation corresponding to each of said plurality of individual packages.

4. The method of analyzing thermal stress according to claim 3, further comprising calculating an amount of warpage deformation corresponding to each of said plurality of individual packages in a temperature atmospheric condition or a load condition by executing said resin flow analysis.

5. The method of analyzing thermal stress according to claim 3, further comprising calculating an amount of warpage deformation corresponding to each of said plurality of individual packages by using values including densities, coefficients of thermal conductivity, coefficients of linear expansion, modulus of elasticity and Poisson's ratio, which are physical property values for each of said resin material, said semiconductor chips and a substrate on which the semiconductor chips are provided, by using a coefficient of linear expansion corresponding to each of said plurality of individual packages, and by using information on binding points and thermal stress load.

6. An analysis processing apparatus, comprising:
    a storage section storing information on physical property values of resin material containing fillers; and
    a control section, when an analysis instruction is inputted, calculating a distribution of the number of said fillers in a composite integrally molded product using said resin material by executing a resin flow analysis using said information stored in said storage section, determining a coefficient of linear expansion of said resin material in said composite integrally molded product based on said distribution of the number of said fillers, and calculating an amount of warpage deformation of said composite integrally molded product by executing a thermal stress analysis using said coefficient of linear expansion as an input condition of physical property values of said thermal stress analysis.

7. The analysis processing apparatus according to claim 6, wherein said control section calculates the number of fillers for each of a plurality of regions by dividing said composite integrally molded product into predetermined regions, by executing said resin flow analysis, when said control section calculates said distribution of the number of said fillers, and
    said control section determines said coefficient of linear expansion corresponding to each of said plurality of regions by referring to data stored in said storage section, indicating a correlation relationship between a filler filling factor and a coefficient of linear expansion when said control section determines said coefficient of linear expansion.

8. The analysis processing apparatus according to claim 6, wherein said composite integrally molded product is a package which comprises a plurality of semiconductor chips and said resin material and,
    said control section divides said package into a plurality of individual packages corresponding to said plurality of semiconductor chips after calculating said amount of warpage deformation of said entire package, and calculates an amount of warpage deformation corresponding to each of said plurality of individual packages.

9. The analysis processing apparatus according to claim 8, wherein said control section further calculates an amount of warpage deformation corresponding to each of said plurality of individual packages in a temperature atmospheric condition or a load condition by executing said resin flow analysis.

10. A method of analyzing resin flow of resin material containing fillers when a component including a substrate and a semiconductor chip is integrally molded by said resin material, the method comprising:
    dividing a space of a die in which said component is placed into a plurality of three-dimensional solid elements according to data of three-dimensional spaces of said component and said die,
    calculating time dependencies of thermal reaction and viscosity of said resin material by substituting physical property values of said resin material, that include at least a density, coefficient of thermal conductivity, specific heat and viscosity, into heat generation equations and viscosity equations,
    calculating a process that shows a flow of said fillers accompanying a flow of said resin material, by substituting information on a filler filling factor and a density of said fillers in said resin material and a diameter of the filler in an initial state when the resin material is placed in a pot, boundary conditions which include at least a temperature of said die, initial temperature of said resin material and a pressure applied to the resin material, and said time dependencies of thermal reaction and viscosity, into an equation of hydrokinetic continuity, Navier-Stokes equations and energy conservation law, and by performing calculation processing corresponding to said plurality of three-dimensional solid elements, calculating the number of said fillers corresponding to each of a plurality of individual packages into which a package is divided, said package being integrally molded with said component by said resin material, by using said process that shows said fillers flowing, calculating a filler filling factor corresponding to each of said plurality of individual packages by using said number of said fillers corresponding to each of said plurality of individual packages, and determining a coefficient of linear expansion according to said filler filling factor, corresponding to each of said plurality of individual packages, by referring to prepared data indicating a correlation relationship between a filler filling factor and a coefficient of linear expansion.

* * * * *